United States Patent [19]
Suhel

[11] 3,973,571
[45] Aug. 10, 1976

[54] CIRCUIT ARRANGEMENT FOR AN AUTOMATIC INTEGRATED INTRAVAGINAL STIMULATOR

[75] Inventor: Peter Šuhel, Ljubljana, Yugoslavia

[73] Assignee: "Gorenje" tovarna gospodinjske opreme, Velenje, Yugoslavia

[22] Filed: Aug. 14, 1975

[21] Appl. No.: 604,815

[30] Foreign Application Priority Data
Aug. 29, 1974  Yugoslavia.......................... 2342/74

[52] U.S. Cl............................... 128/408; 128/422; 331/113 R
[51] Int. Cl.².......................................... A61N 1/36
[58] Field of Search .......... 128/407, 408, 421, 422; 331/111, 113 R

[56] References Cited
UNITED STATES PATENTS

| | | | |
|---|---|---|---|
| 3,241,557 | 3/1966 | Masaki................................ | 128/422 |
| 3,351,872 | 11/1967 | Swift................................ | 331/113 R |
| 3,380,002 | 4/1968 | Hogue.............................. | 331/113 R |
| 3,478,248 | 11/1969 | Ivec................................. | 331/113 R |
| 3,579,139 | 5/1971 | Rhee............................... | 331/113 R |
| 3,800,800 | 4/1974 | Garbe et al......................... | 128/408 |

FOREIGN PATENTS OR APPLICATIONS

| | | | |
|---|---|---|---|
| 1,145,749 | 3/1969 | United Kingdom................ | 128/407 |

*Primary Examiner*—William E. Kamm
*Attorney, Agent, or Firm*—Karl F. Ross; Herbert Dubno

[57] ABSTRACT

An intravaginal stimulator is provided for correcting urinary incontinence which employs a plurality of transistors to form an oscillator with the load formed by the user in series with the battery whereby the circuit is rendered inactive until placed in use.

3 Claims, 1 Drawing Figure

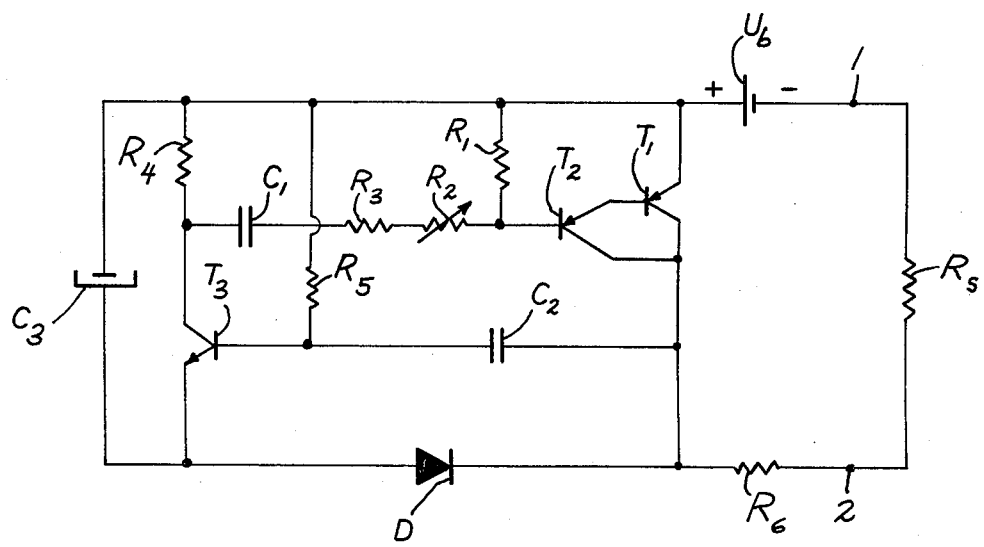

CIRCUIT ARRANGEMENT FOR AN AUTOMATIC INTEGRATED INTRAVAGINAL STIMULATOR

Object of the invention is a circuit arrangement for an automatic integrated intravaginal stimulator intended for stimulators for correcting incontinence at female patients. At the correction of incontinence at female patients the application of functional electrical stimulation is possible for therapeutic as well as permanent correcting aims. With such a stimulator it is possible to correct or to completely stop urinary incontinence, which is a result of physiological or neurophysiological damages.

Beside operational, pharmacological or mechanical correction of incontinence there have hitherto been used different systems applying functional electrical stimulation, such as are a radiofrequency implantable system, an electrical stimulator with a rectal or vaginal insertion and an external unit, and for research aims a percutane electrical stimulation with needle electrodes.

In order to eliminate the need for an external unit, there was set the aim to realize an electrical stimulator simple to use and with which the usage will be therapeutic as well as permanent, and which will be inconspicuous and will, besides, not require an operation.

In order to attain this aim a new electronic circuit arrangement was developed, which is described in detail in the further text and is illustrated in the attached drawing showing its electrical diagram.

As shown in the drawing, to the plus terminal of the battery $U_b$ are connected the emitter of a PNP-transistor $T_1$, one terminal of the resistors $R_1$, $R_4$ and $R_5$ and the positive terminal of the electrolytic capacitor $C_3$. The collector of the transistor $T_1$ together with the collector of the PNP-transistor $T_2$ is connected to one terminal of the capacitor $C_2$ and at the same time to the junction point of the cathode of the diode D and one terminal of the resistor $R_6$. The base of the transistor $T_1$ is connected to the emitter of the transistor $T_2$, whereas the base of the transistor $T_2$ is connected to the junction point of the other terminal of the resistor $R_1$ and one terminal of the variable resistor $R_2$, the other terminal of which is connected to one terminal of the resistor $R_3$. Over the capacitor $C_1$ the other terminal of the resistor $R_3$ is connected to the junction point of the other terminal of the resistor $R_4$ and the collector of the NPN-transistor $T_3$, the base of which is connected to the junction point of the other terminal of the resistor $R_5$ and the capacitor $C_2$ and the emitter of which is connected to the junction point of the negative terminal of the electrolytic capacitor $C_3$ and the anode of the diode D. The negative terminal of the battery $U_b$ is connected with the connector 1 and the other terminal of the resistor $R_6$ with the connector 2. The load $R_s$ is connected between the connector 1 and the connector 2.

The electronic circuit arrangement according to the invention as described in fact represents an astable multivibrator with a highly enlarged ratio pulse-interval, which is attained by means of capacitors $C_1$, $C_2$, by means of resistors $R_1$ to $R_4$ and the diode D. With the adjustable resistor $R_2$ the above-mentioned ratio pulse-interval can be altered and thereby adapted to individual requirements.

A special characteristic of the circuit arrangement according to the invention lies in the fact that it starts to operate automatically immediately when it is loaded with a load $R_s$ with a resistance between 0 and 50 kOhms, which in narrowed limits is represented by the biological resistance of the mucous membrane of the walls of the vagina.

The circuit arrangement according to the invention operates as follows: The voltage of the battery $U_b$ drives a current over the resistor $R_5$ to the base of the transistor $T_3$, because of which the transistor $T_3$ becomes conductive. A consequence of this is that the current now flows on the path from $+U_b$ over the base of the transistor $T_1$, the emitter and the base of the transistor $T_2$, the resistors $R_2$ and $R_3$ and the capacitor $C_1$ to the collector of the transistor $T_3$ and emitter of the transistor $T_3$. The transistors $T_1$ and $T_2$ conduct, and because of this the voltage of the battery $U_b$ drives a current over the resistors of the load $R_s$ and $R_6$. When the voltage on the capacitor $C_1$ has reached a value high enough, the transistors $T_1$ and $T_2$ do not conduct any longer whereafter there appears on the base of the transistor $T_3$ a negative voltage in a value which is approximately the same as the voltage of the battery $U_b$. No current flows through the load any longer, but the capacitor $C_2$, which in the previous phase was charged to an approximate voltage of the battery $U_b$, is discharging with a time-constant $R_5.C_2$. When this voltage on the capacitor $C_2$ reaches a value approximately 0 volts, the transistor starts to conduct again.

The state at which a current flows through the resistor of the load $R_s$ (the mucous membrane of the walls of the vagina) is defined by the time-constant $C_1.(R_1+R_2+R_3)$, whereas the state without current is, as already mentioned, defined by the time-constant $R_5.C_2$. The given system is in an electrically unstable state and the above-mentioned frequency cycle repeats, whereby the frequency time-constants. determined with the sum of tie-constants.

The circuit arrangement can, of course, have small dimensions and can be built into a corresponding stimulator.

What is claimed is:

1. Circuit arrangement for an automatic integrated intravaginal stimulator, characterized in that to the positive terminal of the battery ($U_b$) there is connected the emitter of the transistor ($T_1$), one terminal of the resistors ($R_1$, $R_4$, $R_5$) and the positive terminal of the electrolytic capacitor ($C_3$), and that the collector of the transistor ($T_1$) is together with the collector of the transistor ($T_2$) connected to one terminal of the capacitor ($C_2$) and at the same time to the junction point of the cathode of the diode (D) and one terminal of the resistor ($R_6$), whereby the base of the transistor ($T_1$) is connected to the emitter of the transistor ($T_2$), while the base of the transistor ($T_2$) is connected to the junction point of the other terminal of the resistor ($R_1$) and one terminal of the resistor ($R_2$), the other terminal being connected to one terminal of the resistor ($R_3$), whose other terminal is over the capacitor ($C_1$) connected to the junction point of the other terminal of the resistor ($R_4$) and the collector of the transistor ($T_3$), whose base is connected to the junction point of the other terminal of the resistor ($R_5$) and the capacitor ($C_2$) and whose emitter is connected to the junction point of the negative terminal of the electrolytic capacitor ($C_3$) and the anode of the diode (D), while the negative terminal of the battery ($U_b$) is connected to the connector (1) for the load ($R_s$) and the other terminal of the resistor ($R_6$) is connected to the connector (2) for the load ($R_s$).

2. Circuit arrangement according to claim 1, characterized in that the transistors ($T_1$, $T_2$) are PNP-transistors and that the transistor ($T_3$) is a NPN-transistor.

3. Circuit arrangement according to claim 1, characterized in that the resistor ($R_2$) is a variable resistor.

* * * * *